United States Patent
Ralph et al.

(10) Patent No.: US 7,404,795 B2
(45) Date of Patent: *Jul. 29, 2008

(54) FEMORAL RING LOADER

(75) Inventors: James D. Ralph, Seaside Park, NJ (US); Stephen Tatar, Montvale, NJ (US)

(73) Assignee: SpineCore, Inc., Summit, NJ (US)

( * ) Notice: Subject to any disclaimer, the term of this patent is extended or adjusted under 35 U.S.C. 154(b) by 583 days.

This patent is subject to a terminal disclaimer.

(21) Appl. No.: 10/715,968

(22) Filed: Nov. 18, 2003

(65) Prior Publication Data

US 2004/0102790 A1     May 27, 2004

Related U.S. Application Data

(63) Continuation of application No. 10/075,688, filed on Feb. 13, 2002, now Pat. No. 6,663,638, which is a continuation of application No. 09/844,917, filed on Apr. 27, 2001, now Pat. No. 6,440,142.

(51) Int. Cl.
  *A61B 1/32* (2006.01)
  *A61B 17/58* (2006.01)

(52) U.S. Cl. .......................................... 600/219; 606/99

(58) Field of Classification Search .................. 606/86, 606/99, 90, 61; 623/17.11, 17.16
See application file for complete search history.

(56) References Cited

U.S. PATENT DOCUMENTS

| | | | |
|---|---|---|---|
| 2,167,287 A * | 7/1939 | Witter | 92/196 |
| 3,486,505 A * | 12/1969 | Morrison | 606/90 |
| 5,020,519 A * | 6/1991 | Hayes et al. | 606/237 |
| 5,122,130 A | 6/1992 | Keller et al. | |
| 5,431,658 A * | 7/1995 | Moskovich | 606/99 |
| 5,720,751 A | 2/1998 | Jackson | |
| 5,782,830 A | 7/1998 | Farris | |
| 6,004,326 A | 12/1999 | Castro et al. | |
| 6,066,174 A | 5/2000 | Farris | |
| 6,083,225 A | 7/2000 | Winslow et al. | |
| 6,159,215 A * | 12/2000 | Urbahns et al. | 606/86 |
| 6,174,311 B1 | 1/2001 | Branch et al. | |
| 6,261,296 B1 * | 7/2001 | Aebi et al. | 606/90 |
| 6,267,763 B1 | 7/2001 | Castro | |
| 6,319,257 B1 | 11/2001 | Carignan et al. | |
| 6,440,142 B1 | 8/2002 | Ralph et al. | |
| 6,478,800 B1 * | 11/2002 | Fraser et al. | 606/99 |
| 6,652,533 B2 | 11/2003 | O'Neil | |
| 2001/0010001 A1 | 7/2001 | Michelson | |
| 2002/0099377 A1 | 7/2002 | Zucherman et al. | |
| 2003/0028197 A1 | 2/2003 | Hanson et al. | |
| 2003/0083747 A1 | 5/2003 | Winterbottom et al. | |

* cited by examiner

*Primary Examiner*—Pedro Philogene
(74) *Attorney, Agent, or Firm*—Lerner, David, Littenberg, Krumholz & Mentlik, LLP

(57) ABSTRACT

An instrument for inserting an implant between vertebral bodies, including a holder adapted to hold the implant during insertion of the implant between the vertebral bodies, a retractor adapted to retract the holder away from the implant after the insertion, and a guard adapted to prevent the implant from being removed from between the vertebral bodies during the retraction.

8 Claims, 8 Drawing Sheets

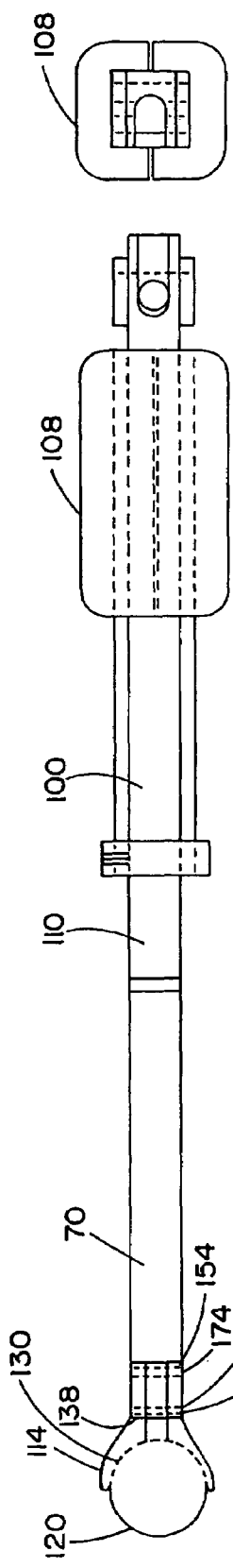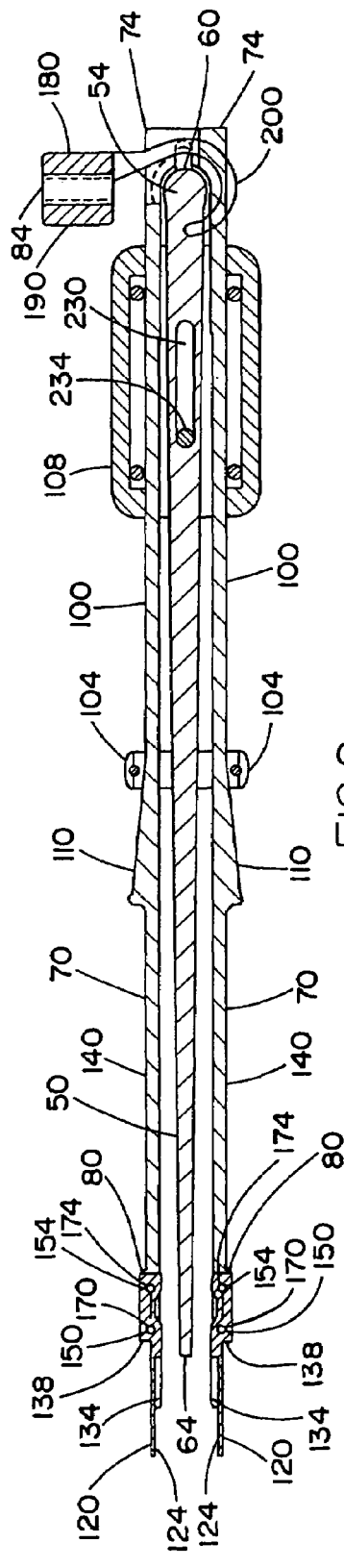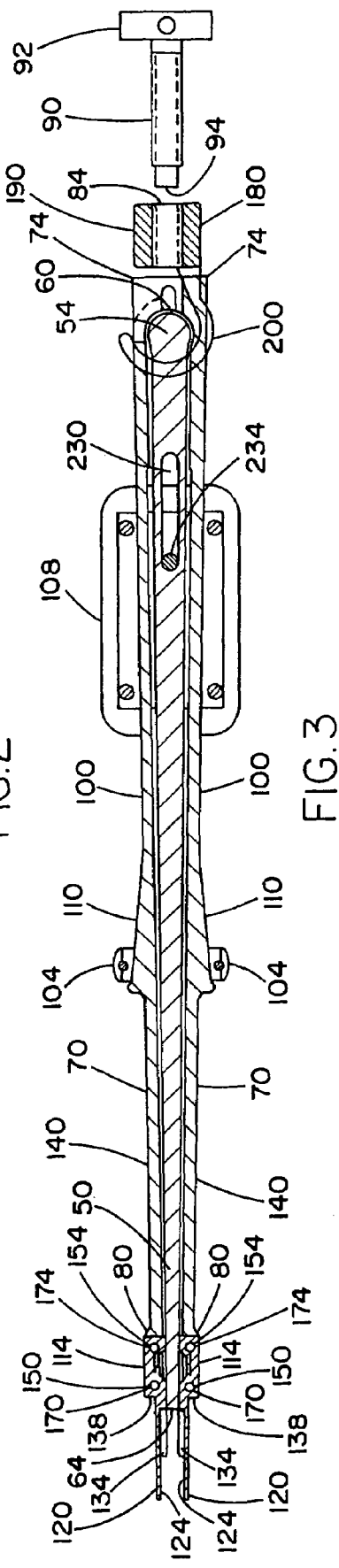

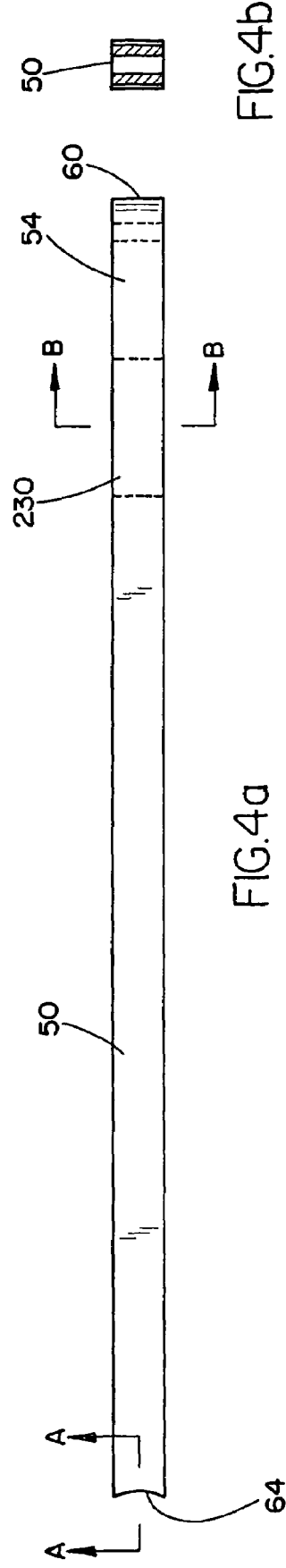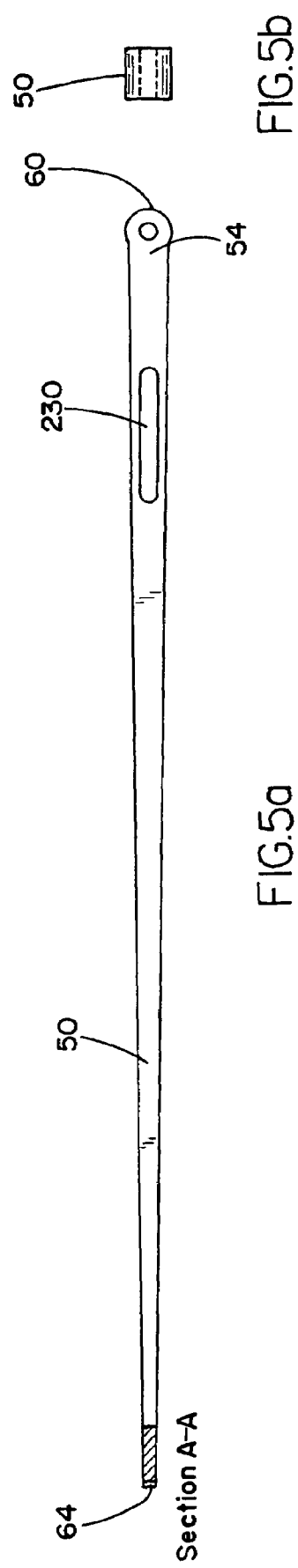

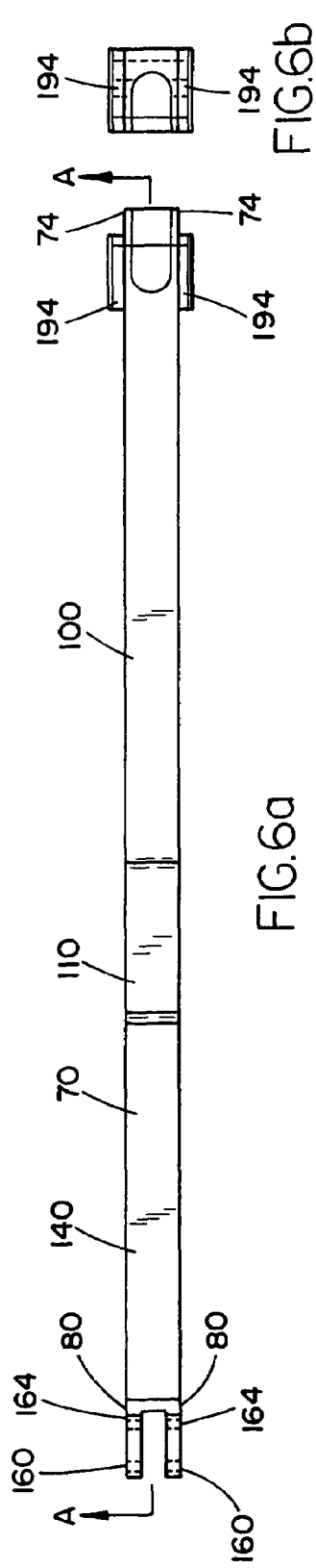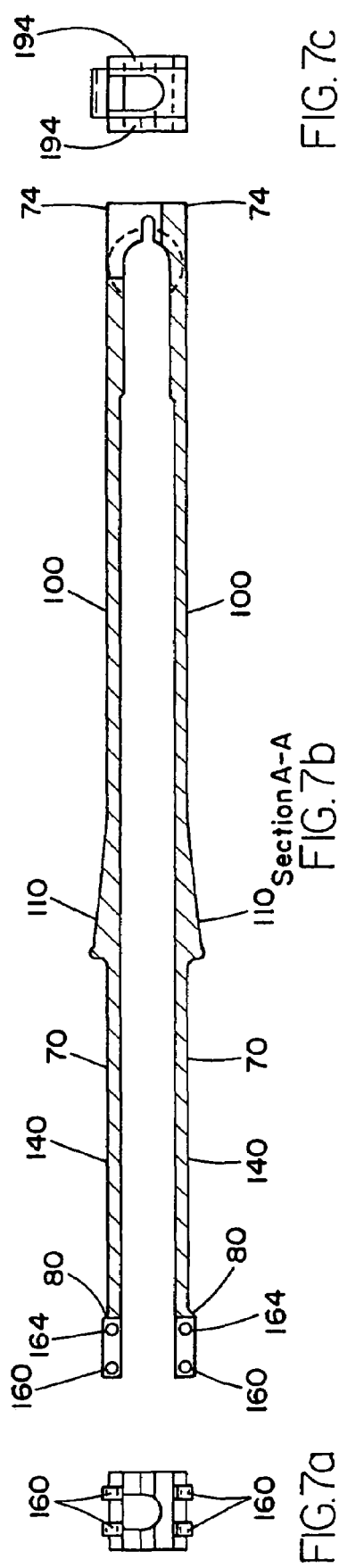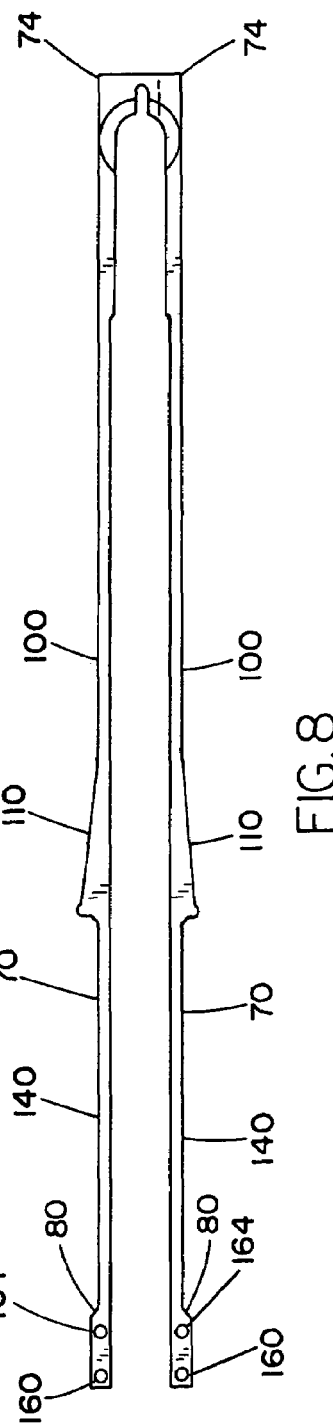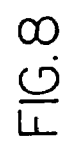

Section A-A

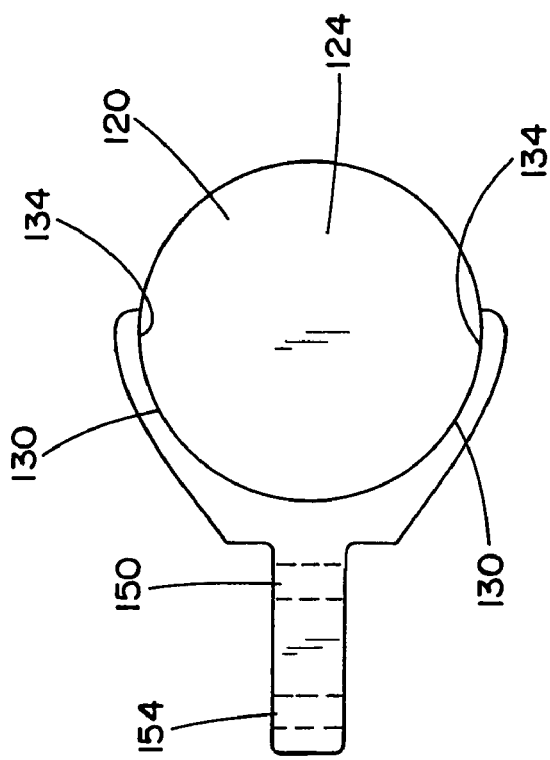
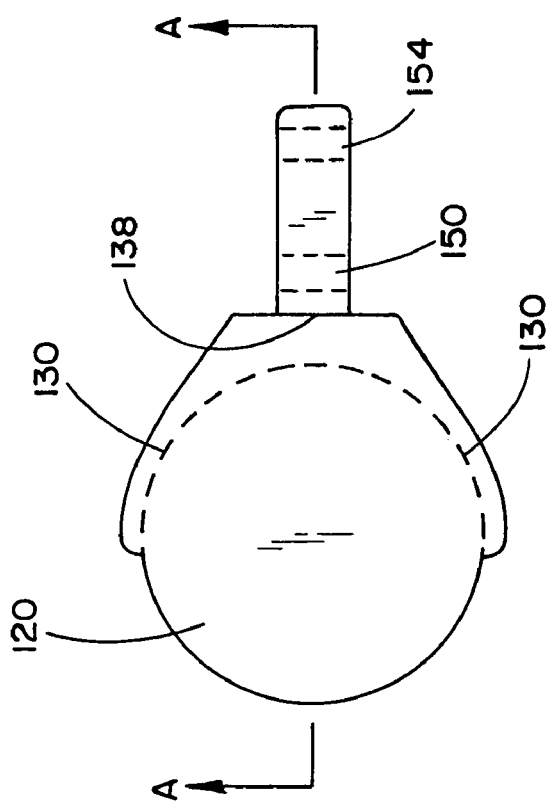
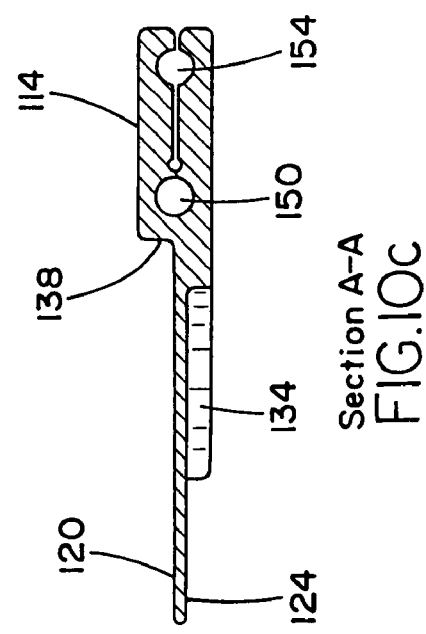
FIG.10b
FIG.10a
Section A-A
FIG.10c

Section A-A

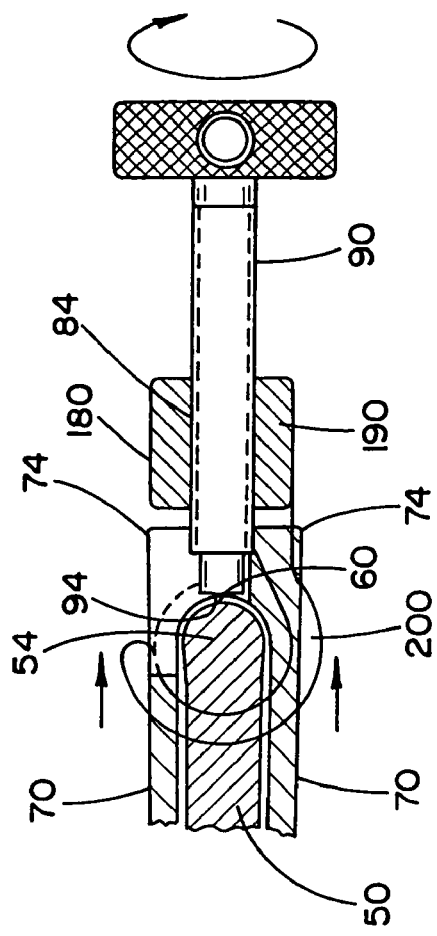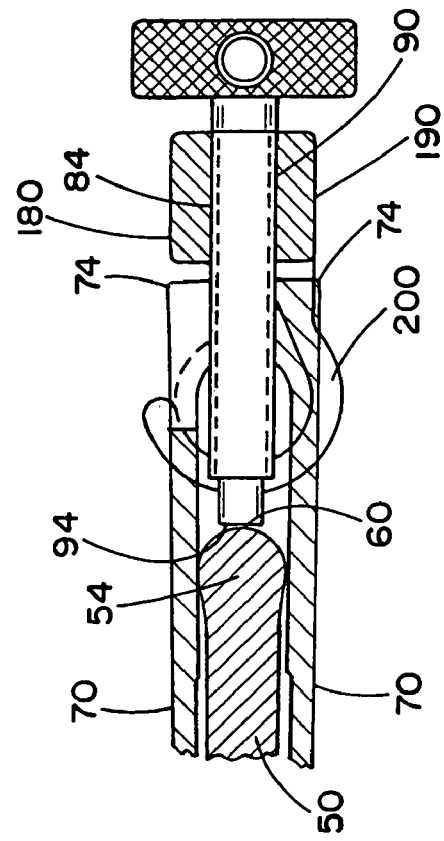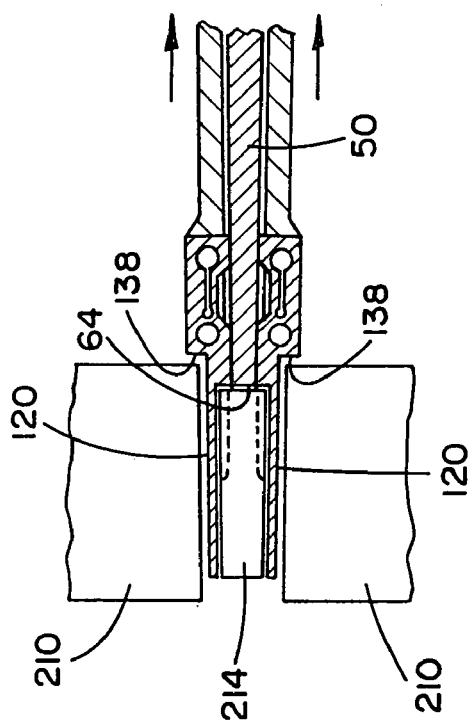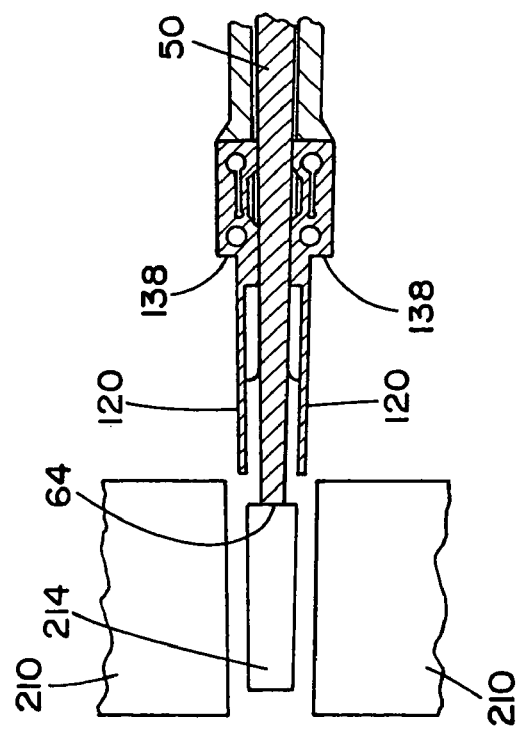
FIG.19　　FIG.20

FEMORAL RING LOADER

CROSS REFERENCE TO RELATED APPLICATION

The present application is a continuing application of U.S. patent application Ser. No. 10/075,688 filed Feb. 13, 2002 entitled "Femoral Ring Loader," now U.S. Pat. No. 6,663,638, which is a continuing application of U.S. patent application Ser. No. 09/844,917 filed Apr. 27, 2001 (now U.S. Pat. No. 6,440,142 issued Oct. 22, 2002) entitled "Femoral Ring Loader."

Implants that can be inserted using the invention include, but are not limited to, femoral ring allografts, bone grafts, vertebral spacers, cylindrical metallic devices (e.g., cages), metal mesh structures that may be filled with suitable bone graft materials, and other implants. Implants that can be inserted using the invention also include a spacer that is described more fully in application, U.S. Ser. No. 10/430,005 to Thomas J. Errico, James D. Ralph and Joseph P. Errico, entitled "Porous Interbody Fusion Device Having Integrated Polyaxial Locking Interference Screws," the disclosure of which is hereby incorporated by reference herein.

FIELD OF THE INVENTION

The invention relates generally to instruments for use in orthopedic surgical implantation procedures and more specifically to an apparatus for inserting an implant between vertebral bodies.

BACKGROUND OF THE INVENTION

The bones and connective tissue of an adult human spinal column consists of more than twenty discrete bones coupled sequentially to one another by a tri-joint complex which consists of an anterior disc and the two posterior facet joints, the anterior discs of adjacent bones being cushioned by cartilage spacers referred to as intervertebral discs. These more than twenty bones are anatomically categorized as being members of one of four classifications: cervical; thoracic; lumbar; or sacral.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, and the insertion of implants and/or height restorative devices, several methods and devices have been disclosed in the prior art.

More particularly, and with respect to the historical development of the present surgical methods and instrumentations, the description of the relevant medical techniques are now described. Failure of the intervertebral disc cartilage generally includes a loss of proper anatomical spacing between the end plates of the opposing vertebral bodies. This loss of height may simply destabilize the spine, or, in severe cases, it may cause considerable neurological impairment as the nerve roots are compressed by the converging lateral extensions of the bones (e.g., in the facet joint).

Restoring the appropriate height to the intervertebral space is the first step in the surgical strategy for correcting this condition. Once this is achieved, one class of surgical implantation procedures involves positioning a device into the intervening space. This may be done through a posterior approach, a lateral approach, or an anterior approach. Various implant devices for this purpose include femoral ring allograft, cylindrical metallic devices (e.g., cages), and metal mesh structures that may be filled with suitable bone graft materials. Some of these implant devices are only suitable for one direction of approach to the spine. All of these devices, however, are provided with the intention that the adjacent bones will, once restored to their appropriate separation, then grow together across the space and fuse together (or at least fuse into the device implanted between the bones).

Most recently, the development of non-fusion implant devices, which purport to permit continued natural movement in the tri-joint complex, have provided great promise. The instrumentation and methods for the implantation of these non-fusion devices, as well as the implantation of the fusion devices catalogued previously, therefore should integrate the functions of restoring proper anatomical spacing and easing insertion of the selected device into the formed volume.

To these ends, several instruments for such implantation have been described in the prior art. These include U.S. Pat. No. 6,159,215 to Urbahns, et al. ("Urbahns"), U.S. Pat. No. 6,042,582 to Ray ("Ray"), and U.S. Pat. No. 5,431,658 to Moskovich ("Moskovich"). More particularly, Ray describes a device and method of implantation for use specifically with cylindrical cage devices that are inserted such that the axis of the implant device is perpendicular to the axis of the spine. The reference teaches the use of a series of similarly shaped plugs to be inserted posteriorly between the collapsed bones, for the purposes of separating the adjacent bones, followed by the cutting of the endplates to receive the threaded implant.

Urbahns teaches the use of intervertebral space measuring tools and a spacer insertion device for facilitating the implantation of an intervertebral spacer (in this reference, the spacer implant is a tubular metal mesh structure which is coaxial with the patient's spine). The measuring device described and shown in FIG. 4 in Urbahns includes a thin, elongate rod having a fixed cylindrical end having a constant and known thickness. Insertion of this measuring tool into the intervertebral space provides the physician with an approximate understanding of the size of the implant to be inserted. This measurement defines the appropriate cutting of the patient's bone to create the desired, and necessary, space to receive the metal mesh. The measuring tool is, however, not used to distract the space.

Urbahn describes a distraction provided in conjunction with the spacer insertion instrument shown in FIGS. 13-16 of the reference. This instrument, which is more fully described and shown in FIG. 4 in Moskovich, includes a pair of flat elongate guide surfaces that are hinged at an elbow joint at the distal ends of the surfaces. The distal joint is designed to extend out of the planes defined by the longitudinal axes of the two guides. The proximal ends of the surfaces are to be placed between the collapsed bones. By virtue of the elbow joint, the surfaces are angled substantially when the metal mesh structure, or test member, is placed between the surfaces. The metal mesh (or the test member) is then hammered down the guide surfaces, prying the vertebral bodies apart.

Moskovich is generally directed to a threaded insertion device for final placement of the femoral ring (not a metal mesh structure) into the intervertebral space. A threaded shaft, having a distal ram portion and an intermediate nut, is coupled to the guide surfaces via stud-groove interfaces that engage studs on the intermediate nut and corresponding grooves on the elongate guide surfaces. The ram portion seats against the femoral ring and causes it to move relative to the guides. The space into which the femoral ring is to be inserted (as above with the metal mesh implant) must be cut to the appropriate size to receive the graft. Initially, the surgeon rotateably advances the graft into the space. Subsequent to proper placement of the graft (i.e., when the graft jams into the pre-cut receiving space), continued rotation of the shaft causes the distraction surfaces to be removed by motion of the guides relative to the shaft (the intermediate nut engages the guides and pulls them free of the vertebral bones). Failure to properly cut the space, or structural failure of the graft and/or bone material, will prevent removal of the guides, and further rotation of the shaft will drive the allograft further than clinically desired (risking paralysis and/or damage to surrounding vessels).

Therefore, there is a need for a vertebral implant insertion device that does not require the space into which the implant is to be inserted to be cut to a specific size or shape so that the implant must jam into the space to effect the removal of the guides. There is also a need for an insertion device that does not increase the risk of structural failure of the implant during the insertion and does not depend on the structural stability of the implant to effect the insertion.

SUMMARY OF THE INVENTION

In an embodiment, the invention provides an instrument for inserting an implant between vertebral bodies. The instrument includes a holder adapted to hold the implant during insertion of the implant between the vertebral bodies, a retractor adapted to retract the holder away from the implant after the insertion, and a guard adapted to prevent the implant from being removed from between the vertebral bodies during the retraction.

In an aspect, the retractor can include a coupling adapted to couple the holder to the guard and by which relative movement between the holder and the guard can be effected during the retraction. Preferably, the retractor includes a threaded coupling that includes a bore and a screw that can thread within the bore, such that rotation of the screw within the bore effects relative movement between the holder and the guard.

In another aspect, the holder can include a plurality of arms. The guard can include a shaft adjacent the arms, the shaft having an engagement surface. The retractor can include a threaded bore and a screw that can thread within the bore, the screw having an end that engages the engagement surface of the shaft. Preferably, rotation of the screw within the bore moves the arms relative to the shaft.

In still another aspect, the guard can include a shaft having a proximal end and a distal end. The holder can include a plurality of arms, each having a distal end, the arms being adapted to cooperate to hold the implant using the distal ends of the arms such that the implant is adjacent the distal end of the shaft. The retractor can include a bore and a screw that can thread within the bore and engage the proximal end of the shaft. Preferably, rotation of the screw within the bore effects the retraction by pulling the arms alongside the shaft; and during the retraction, the distal end of the shaft can engage the implant to prevent the implant from being removed from between the vertebral bodies.

In yet another aspect, the guard can include a shaft having a longitudinal axis, a proximal end having an engagement surface, and a distal end. The holder can include a plurality of arms, each having a proximal end and a distal end and each longitudinally extending alongside the shaft, the arms being adapted to cooperate to hold the implant using the distal ends of the arms such that the implant is longitudinally adjacent the distal end of the shaft during insertion of the implant between the vertebral bodies. The retractor can include a bore in longitudinally fixed relation to the arms during the retraction and having a longitudinal axis coaxial with the longitudinal axis of the shaft during the retraction, and a screw that can thread within the bore and having a distal end that engages the engagement surface of the proximal end of the shaft during the retraction. Preferably, rotation of the screw within the bore, after the insertion of the implant between the vertebral bodies and once the distal end of the screw has engaged the engagement surface of the shaft, effects the retraction by pulling the arms alongside the shaft until the distal ends of the arms no longer hold the implant. Also preferably, during the retraction, the distal end of the shaft can engage the implant to prevent the implant from being removed from between the vertebral bodies.

Preferably, the distal ends of the arms can be opened away from one another to receive the implant, and closed toward one another to hold the implant. Also preferably, the proximal ends of the arms are joined to one another. Also preferably, each arm has an outer surface, and the instrument further includes a collar that can be slid against the outer surfaces of the arms to open and close the distal ends of the arms. Also preferably, each of the outer surfaces has a laterally outwardly tapering portion against which the collar can be slid.

Preferably, each of the distal ends of the arms includes an extension that extends beyond the distal end of the shaft, and the implant is held between the extensions. Also preferably, each extension includes a plate having a surface that contacts the implant when the implant is held. Also preferably, each plate has a lateral edge and a lateral guard at the edge to prevent the implant from laterally moving from between the plates when the implant is held. Also preferably, during the insertion, the plates can be inserted between the vertebral bodies with the implant between the plates, and during the retraction, the plates can be removed from between the vertebral bodies by the retractor. Also preferably, at least one of the extensions has a ridge for limiting the extent to which the plate of the extension can be inserted between the vertebral bodies during the insertion.

Preferably, the distal ends of the arms are adapted to adjust to accommodate the surface topography of the implant to hold the implant. Also preferably, each of the arms includes a longitudinally extending body and each of the distal ends of the arms includes an extension and a coupling whereby the extension is coupled to the body so that the extension can hinge relative to the body. Also preferably, the coupling includes a distal lateral through hole on the extension, a proximal lateral through slot on the extension, a distal lateral through hole on the body, a proximal lateral through hole on the body, a distal rod passing laterally through the distal through holes, and a proximal rod passing laterally through the proximal through hole and the proximal through slot. Also preferably, the through slot can expand to allow the extension to hinge relative to the body.

Preferably, the retractor includes a body having the bore and a coupling whereby the body is coupled to the proximal ends of the arms so that the body can hinge relative to the arms to place the bore in longitudinally fixed relation to the arms during the retraction and to align the longitudinal axis of the bore coaxial with the longitudinal axis of the shaft during the retraction. Also preferably, the coupling enables the body to hinge relative to the arms to allow access to the proximal end of the shaft. Also preferably, the body includes a trunk having the bore and the coupling includes at least one curved passageway fixed to the proximal ends of the arms and at least one corresponding hook fixed to the trunk, whereby the travel of the hook through the passageway provides a range of positions through which the trunk can hinge relative to the arms. Also preferably, one of the positions is a position in which the bore is in longitudinally fixed relation to the arms and the longitudinal axis of the bore is aligned coaxial with the longitudinal axis of the shaft. Also preferably, another of the positions is a position in which the trunk is positioned to allow access to the proximal end of the shaft.

In another embodiment, the invention again provides an instrument for inserting an implant between vertebral bodies. The instrument includes a holder adapted to hold the implant during insertion of the implant between the vertebral bodies, a retractor adapted to retract the holder away from the implant after the insertion, and a guard adapted to prevent the implant from being removed from between the vertebral bodies during the retraction.

In an aspect, the holder can include a set of tongs adapted to hold the implant. The guard can include a central rod about which the set of tongs open and close. The retractor can include a screw assembly for retracting the set of tongs away from the implant while maintaining the rod against the implant to prevent the implant from being removed from between the vertebral bodies. Preferably, the screw assembly includes a bore and a screw that can be rotated within the bore to engage the rod during the retraction and move the set of tongs relative to the shaft.

In another aspect, the holder can include a set of tongs having a proximal end and distal ends for holding the implant during the insertion of the implant between the vertebral bodies. The guard can include a central rod about which the set of tongs can open and close, the rod having a proximal end and a distal end in front of which the distal ends of the set of tongs can hold the implant during the insertion, the rod being coupled to the set of tongs to prevent lateral movement between the rod and the set and allow longitudinal movement between the rod and the set. The retractor can include a screw assembly at the proximal end of the set of tongs adapted to retract the distal ends of the set of tongs away from the implant after the insertion while allowing the distal end of the rod to be maintained against the implant during the retraction to prevent the implant from being removed from between the vertebral bodies during the retraction. Preferably, the screw assembly includes a bore longitudinally fixed to the set of tongs during the retraction and aligned with the rod during the retraction, and a screw that can be rotated within the bore to engage the proximal end of the rod during the retraction and pull the set of tongs longitudinally relative to the shaft until the distal ends of the set of tongs no longer hold the implant. Preferably, the screw can thread within the bore.

Preferably, the rod is coupled to the set of tongs by a coupling including a lateral through slot through the rod that extends longitudinally within the rod, and a pin on the set of tongs that passes laterally through the through slot and travels longitudinally within the through slot during the retraction.

Preferably, the screw assembly is coupled to the proximal end of the set of tongs so that the screw assembly can hinge relative to the set of tongs through a range of positions including a position in which the bore is longitudinally fixed to the set of tongs and aligned with the rod, and a position in which the proximal end of the rod can be accessed.

Implants that can be inserted using the invention include, but are not limited to, femoral ring allografts, bone grafts, vertebral spacers, cylindrical metallic devices (e.g., cages), metal mesh structures that may be filled with suitable bone graft materials, and other implants. Implants that can be inserted using the invention also include a spacer that is described more fully in copending application, U.S. Ser. No. 10/430,005, to Thomas J. Errico and Joseph P. Errico, entitled "Porous Interbody Fusion Device Having Integrated Polyaxial Locking Interference Screws", the specification of which is incorporated herein by reference.

BRIEF DESCRIPTION OF THE DRAWINGS

FIGS. 1a-b are top and back views of an embodiment of the invention, respectively, showing an instrument with the arms open and without the retractor;

FIG. 2 is a side cutaway view of the embodiment, with the arms open and the body of the retractor positioned to allow access to the proximal end of the shaft;

FIG. 3 is a side cutaway view of the embodiment, with the arms closed and the body of the retractor positioned so that the bore is coaxial with the shaft, and showing the screw of the retractor positioned for insertion into the bore;

FIGS. 4a-b are top and cutaway (along line B-B in FIG. 4a) views of the shaft, respectively;

FIGS. 5a-b are side (showing a partial section along line A-A in FIG. 4a) and back views of the shaft, respectively;

FIGS. 6a-b are top and back views of the arms, respectively;

FIGS. 7a-c are front, side cutaway (along line A-A in FIG. 6a), and back views of the arms, respectively;

FIG. 8 is a side view of the arms;

FIGS. 10a-c are top, bottom and side cutaway (along line A-A in FIG. 10a) views of the extension of the distal end of one of the arms, respectively;

FIGS. 19-20 show an exemplary retraction of the distal ends of the arms.

DETAILED DESCRIPTION OF THE PREFERRED EMBODIMENT

Figure 9C:
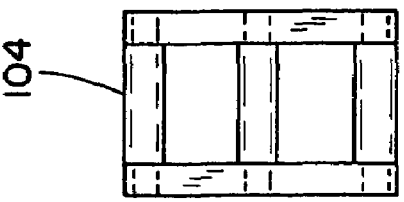
FIGS. 9a-c are top, side cutaway (along line A-A in FIG. 9a), and back views of the collar, respectively.

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

An embodiment of the invention is now described in detail and shown in the accompanying figures as an instrument for inserting an implant between vertebral bodies. The instrument includes a holder adapted to hold the implant during insertion of the implant between the vertebral bodies, a retractor adapted to retract the holder away from the implant after the insertion, and a guard adapted to prevent the implant from being removed from between the vertebral bodies during the retraction.

Referring now to FIGS. 2, 3, 4a-b, and 5a-b, the guard includes a shaft 50 that has a longitudinal axis, a proximal end 54 that has an engagement surface 60, and a distal end 64. The shaft 50 is tapered to have a narrower cross-section at the distal end 64 than at the proximal end 54. The distal end 64 has a curved surface.

Referring now to FIGS. 1a-b, 2, 3, 6a-b, 7a-c, and 8, the holder includes a plurality of arms 70, each having a proximal end 74 and a distal end 80. Each of the arms 70 longitudinally extends alongside the shaft 50.

Referring now to FIGS. 2, 3, 11a-c and 12, the retractor includes a bore 84 having a longitudinal axis and a screw 90 that can thread within the bore 84. The screw 90 has a head 92 and a distal end 94.

Referring again to FIGS. 2-3, the arms 70 are adapted to cooperate to hold the implant using the distal ends 80 of the arms 70 such that the implant is longitudinally adjacent the distal end 64 of the shaft 50. More specifically, the proximal ends 54 of the arms 70 are joined to one another, and the distal ends 80 of the arms 70 can be opened away from one another (as shown in FIG. 2) to receive the implant, and closed toward one another (as shown in FIG. 3) to hold the implant.

Figure 9A:
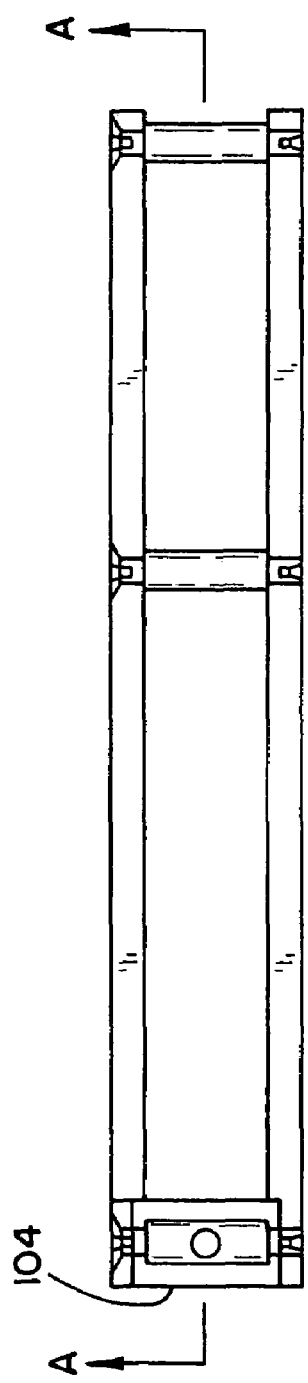
Figure 9B:
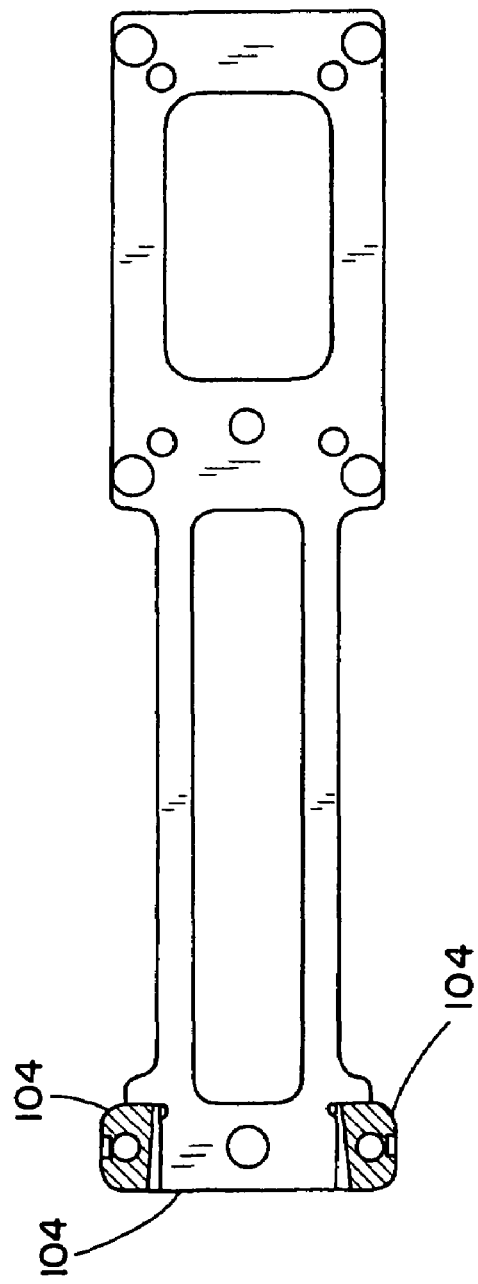
Figure 11A:
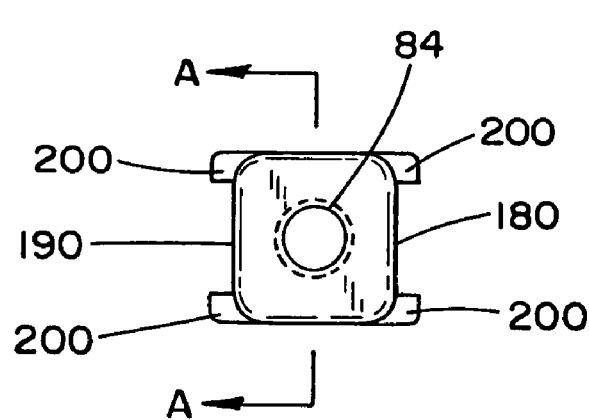
FIGS. 11a-c are top, cutaway (along line A-A in FIG. 11a) and side views of the body of the retractor, respectively.
Figure 12:
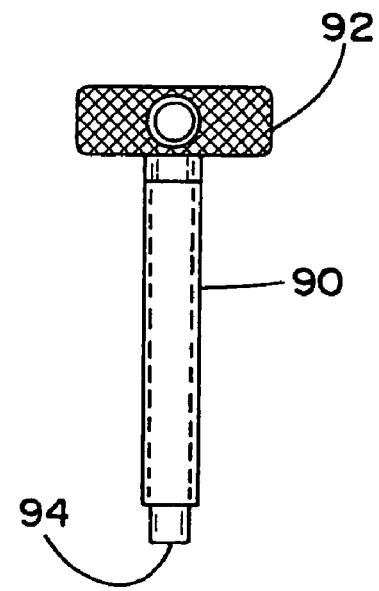
FIG. 12 is a side view of the screw of the retractor.
Figure 11B:
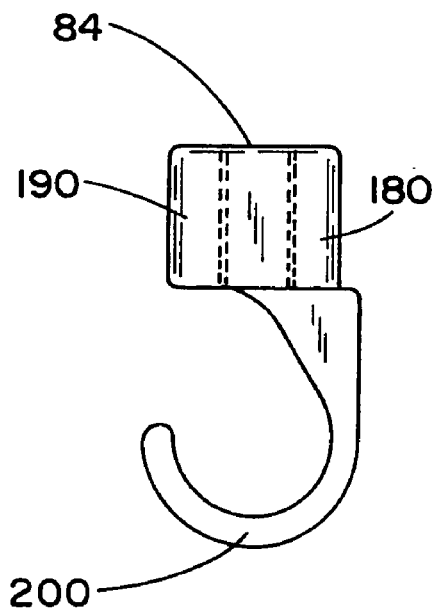
Figure 11C:
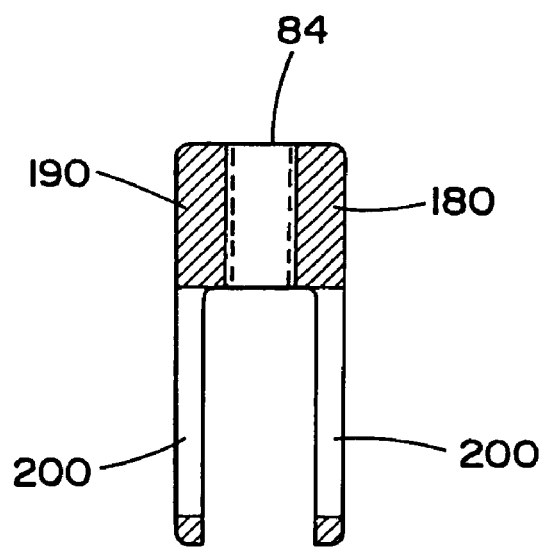
Figure 13:
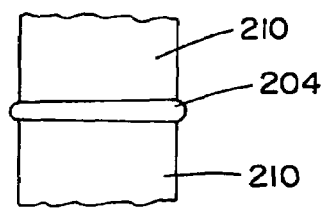
FIGS. 13-14 show damaged or unwanted tissue between vertebral bodies and clearance of the same.
Figure 14:
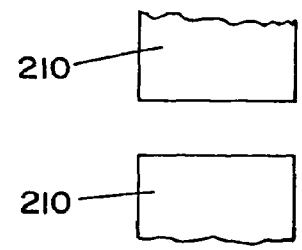
Figure 15:
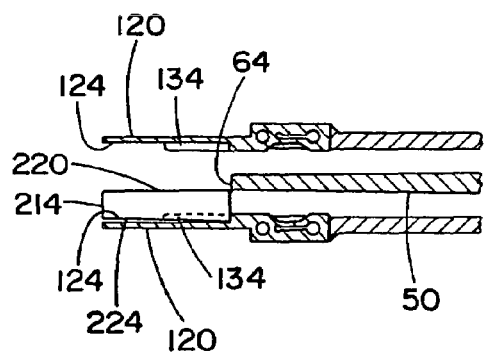
FIGS. 15-16 show an exemplary receipt of an implant by the instrument.
Figure 16:
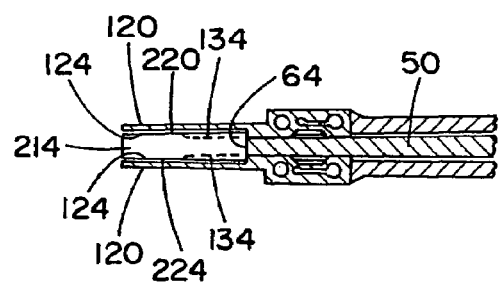

Further in this regard, referring again to FIGS. 1a-b, 2, 3, 6a-b, 7a-c, and 8, and referring also to FIGS. 9a-c, each arm 70 has an outer surface 100, and the instrument further includes a laterally rigid collar 104 that can be slid against the outer surfaces 100 of the arms 70 to open and close the distal ends 80 of the arms 70. More specifically, each of the outer surfaces 100 has a laterally outwardly tapering portion 110 against which the collar 104 can be slid. Accordingly, the imposition of the collar 104 against the tapered portions 110 causes the arms 70 to be forced toward the shaft 50. The taper of the shaft 50 accommodates this movement of the arms 70. The instrument further includes a handle 108 that is attached to the collar 104 and that can be used to slide the collar 104.

Further in this regard, referring again to FIGS. 1a-b, 2, and 3, and referring also to FIGS. 10a-c, each of the distal ends 80 of the arms 70 includes an extension 114 that extends beyond the distal end 64 of the shaft 50, and the implant can be held between the extensions 114 when the distal ends 80 are closed. Each extension includes a plate 120 having a surface 124 that contacts the implant when the implant is held. Each plate 120 has a lateral edge 130 and a lateral guard 134 at the edge 130 to prevent the implant from laterally moving from between the plates 120 when the implant is held. Each extension 114 has a ridge 138 that prevents the plates 120 and the implant from being inserted further in between the vertebral bodies than clinically desired, as described in greater detail below.

The distal ends 80 of the arms 70 are adapted to adjust to accommodate the surface topography of the implant to hold the implant. The implant to be inserted typically has a surface topography such that an upper surface of the implant is substantially parallel to a lower surface of the implant. However, for some clinical applications, the implant may have a tapered surface topography such that an upper surface of the implant is not substantially parallel to a lower surface of the implant. This embodiment and other embodiments of the invention accommodate such varied surface topographies to hold either type of implant for insertion.

In this regard, referring again to FIGS. 2, 3, 6a-b, 7a-c, 8, and 10c, each of the arms 70 includes a longitudinally extending body 140. Each of the distal ends 80 of the arms 70 includes the extension 114 and a coupling whereby the extension 114 is coupled to the body 140 so that the extension 114 can hinge relative to the body 140. In this regard, the coupling includes a distal lateral through hole 150 on the extension 114 and a proximal lateral through slot 154 on the extension 114. The coupling further includes a distal lateral through hole 160 on the body 140 and a proximal lateral through hole 164 on the body 140. The coupling further includes a distal rod 170 passing laterally through the distal through holes 150, 160. The coupling further includes a proximal rod 174 passing laterally through the proximal through hole 150 and the proximal through slot 154. The through slot 154 can expand to allow the extension 114 to hinge relative to the body 140. The through slot 154 permits the expansion but is biased toward not expanding. This feature of the through slot 154 can be provided by constructing the extension 114 using a material that provides structural stability but which has some elasticity to permit the expansion when stressed. Suitable materials include, but are not limited to, surgical steel and titanium.

Referring again to FIGS. 2, 3, 6a-b, 7c, 11a-c, and 12, the retractor includes a body 180 having the bore 84 and a coupling whereby the body 180 is coupled to the proximal ends 74 of the arms 70 so that the body 180 can hinge relative to the arms 70. The coupling enables the bore 84 to be placed in longitudinally fixed relation to the arms 70 so that if the bore 84 is moved longitudinally, the arms 70 will also move with the bore 84. The coupling also enables the longitudinal axis of the bore 84 to be aligned coaxial with the longitudinal axis of the shaft 50. This alignment permits the screw 90 to be used to effect the retraction, as described in greater detail below. The coupling also enables the body 180 to hinge relative to the arms 70 to allow access to the proximal ends 74 of the arms 70. Such access may be required during the insertion procedure, as described in greater detail below.

In this regard, the body 180 includes a trunk 190 having the bore 84 and the coupling includes two curved passageways 194 fixed to the proximal ends 74 of the arms 70 and corresponding hooks 200 fixed to the trunk 190. The travel of the hooks 200 through the passageways 194 provides a range of positions through which the trunk 190 can hinge relative to the arms 70. One of the positions (shown, e.g., in FIG. 3) is a position in which the bore 84 is in longitudinally fixed relation to the arms 70 and the longitudinal axis of the bore 84 is aligned coaxial with the longitudinal axis of the shaft 50. Another of the positions (shown, e.g., in FIG. 2) is a position in which the trunk 190 is positioned to allow access to the proximal end 54 of the shaft 50.

Further in this embodiment, and referring again to FIGS. 2-3, the shaft 50 is coupled to the arms 70 to prevent lateral movement between the shaft 50 and the arms 70 and allow longitudinal movement between the shaft 50 and the arms 70. In this regard, the coupling between the shaft 50 and the arms 70 includes a lateral through slot 230 through the shaft 50 that extends longitudinally within the shaft 50, and a pin 234 attached to the arms 70 that passes laterally through the through slot 230 and travels longitudinally within the through slot 230 during the retraction. This feature facilitates the longitudinal movement of the arms 70 with respect to the shaft 50 while helping to maintain the stability of the instrument during use.

A use of the instrument will now be described with additional reference to FIGS. 13-20. The surgeon first prepares the vertebral column for insertion of the implant. The surgeon clears away any damaged or unwanted tissue 204 from between the vertebral bodies 210 between which the implant is to be inserted. The surgeon then expands the space between the vertebral bodies 210 enough to accommodate the implant which is to be inserted. Any suitable method for expanding the space in this regard can be used, including methods known in the art.

It should be noted that the instrument of the invention is used after the space between the vertebral bodies 210 has been expanded sufficiently to accommodate the implant which is to be inserted. While during the insertion using the instrument some expansion of the space will be effected in many cases due to forces exerted by the surgeon, the instrument is not used primarily for expanding the space prior to the insertion.

It should also be noted, although this aspect of the invention is described in greater detail below, that the vertebral bodies 210 do not need to be cut in any specific manner, and the space does not otherwise need to be prepared, in order for the instrument of the invention to effectively insert the implant and remove the holder. Specifically, for example, there is no need to cut the vertebral bodies 210, or otherwise prepare the space, so that the implant jams into the space. Novel features and methods of the invention are disclosed herein for avoiding the need for such activities and events.

The surgeon then operates the instrument to hold the implant 214 between the plates 120. The surgeon prepares the instrument for receiving the implant 214 by placing the collar 104 in a proximal position that allows the arms 70 to open (FIG. 2). In this position, as shown in magnified view in FIG. 15, the plates 120 are open and the surgeon places the implant 214 on the lower plate 120. The lateral guard 134 on the lower plate 120 prevents the implant 214 from slipping off the lower plate 120 as the surgeon continues to operate the instrument. Once the implant 214 is placed on the lower plate 120, the surgeon moves the collar 104 to a distal position that closes the arms 70 (FIG. 3). In this position, as shown in magnified view in FIG. 16, the implant 214 is held between the plates 120.

Movement of the collar 104 from the proximal position to the distal position causes the collar 104 to engage the laterally outwardly tapering portions 110 of the outer surfaces 100 of the arms 70. Because the collar 104 is laterally rigid, and the tapering portions 110 gradually increase the thickness of the arms 70, the engagement of the collar 104 with the tapering portions 110 forces the arms 70 toward the shaft 50. The taper of the shaft 50 accommodates this movement of the arms 70. The surgeon is able to move the collar 104 by gripping the handle 108 and sliding the handle 108 toward the proximal ends 74 of the arms 70 or toward the distal ends 80 of the arms 70.

As the plates 120 close on the implant 214, the plates 120 adjust to the topography of the implant 214. More specifically, as the plates 120 close on the implant 214, each of the contact surfaces 124 of the plates 120 seeks to rest flat against the corresponding surfaces of the implant 214. Whether or not the upper and lower surfaces 220, 224 of the implant 214 are parallel, the plates 120 are able to move to positions in which the contact surfaces 124 rest flat against the corresponding surfaces 220, 224 of the implant 214. In this regard, as the plates 120 close on the implant 214, the extensions 114 hinge about the distal rods 170 and, if necessary, the through slots 154 expand as the proximal rods 174 press against the inner surface of the through slots 154. As noted above, the extensions 114 in this embodiment and other embodiments are formed from a material having some elasticity so as to permit the expansion but be biased toward not expanding. This ensures that even as the through slots 154 expand, the extensions 114 provide structural support for holding the implant 214.

When the implant 214 is held between the plates 120, the lateral guards 134 of the plates 120 prevent the implant 214 from exiting laterally from between the plates 120.

Figure 17:
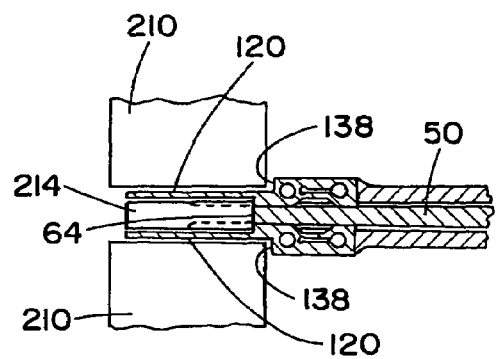
FIG. 17 shows an exemplary insertion of the implant in between the vertebral bodies using the instrument.

As shown in FIG. 17, the surgeon then inserts the plates 120 between the vertebral bodies 210 with the implant 214 between the plates 120. The surfaces of the plates 120 in this embodiment and other embodiments are micromachined to be extremely smooth so that the insertion can be accomplished with a minimum of force and a minimum of collateral damage. The surgeon can grip the handle 108 and push the instrument to insert the plates 120 and the implant 214 in between the vertebral bodies 210. During the insertion, the lateral guards 134 of the plates 120 press against the implant 214 (depending on the direction of insertion) to assist in urging the implant 214 in between the vertebral bodies 210, and prevent the implant 214 from exiting laterally from between the plates 120.

It should be noted that it is not necessary for the shaft 50 to act as a ram to push the implant 214 in between the vertebral bodies 210. Nor is the screw 90 rotated to use the shaft 50 in such a manner. The use of the screw 90 is described below, and is for retracting the plates 120, not for pushing the implant 214. The implant 214 is held between the plates 120, and the arms 70 provide structural support as the surgeon pushes the arms 70 to insert the implant 214 and the plates 120 in between the vertebral bodies 210. During the pushing, the lateral guards 134, and primarily the most proximal portions of the lateral guards 134, press against the implant 214 to help urge the implant 214 in between the vertebral bodies 210 along with the plates 120.

It should also be reiterated that other than the expansion of the space between the vertebral bodies 210 to accommodate the implant 214, neither the vertebral bodies 210 nor the space must be prepared for proper insertion of the implant 214 and the plates 120, and effective removal of the plates 120 after the insertion. There is no need to cut the vertebral bodies 210 so that the implant 214 jams in the space. The instrument of the invention in this embodiment and other embodiments is adapted to prevent the implant 214 from being inserted further than is clinically desirable even if the dimensions of the space will not cause the implant 214 to jam in between the vertebral bodies 210. The ridges 138 limit the extent to which the plates 120 can be inserted between the vertebral bodies 210 during the insertion, because the ridges 138 will contact the sides of the vertebral bodies 210 if the surgeon attempts to insert the plates 120 further than is clinically desirable.

It should also be noted that an instrument of the invention can include alternative or additional ridges or protrusions to prevent the implant from being inserted further than is clinically desirable. Such protrusions could also assist the surgeon in maintaining the placement of the implant during the retraction of the holder. For example, the guard could have one or more protrusions that can rest against the side or sides of the vertebral body or bodies during the retraction of the holder. This would be useful, for example, to allow the surgeon to press the protrusion or protrusions against the side or sides to ensure that the placement of the implant is maintained as the holder is retracted. Otherwise, the surgeon must be sure to not move the guard during the retraction, or to at least minimize movement of the guard during the retraction, to ensure that the placement of the implant is maintained. This may be difficult because the surgeon may not have anything to serve as a guide to hold the guard in the same place. Such protrusions on the guard may assist the surgeon by serving as a guide in this manner. As a specific example with regard to the presently described embodiment, the shaft 50 can include one or more ridges or other protrusions near or at its distal end 64 that protrude far enough out from the shaft 50 to engage the side (or sides) of the vertebral body (or bodies) 210 if the surgeon attempts to insert the plates 120 further than is clinically desirable. In this regard, if two ridges or protrusions are desirable, each arm 70 can include a slot through which a ridge of the shaft 50 is accommodated when the arms 70 are closed and not retracted. Each slot could extend through the extension 114 all the way through the plate 120. Therefore, each extension 114 could be partially split by the slot. Each half of each extension 114 could still have enough surface area on its half-plate and enough structural stability to hold the implant 214, because the halves of the extension 114 could be secured to one another aft of the plate 120 but forward of the distal end 80 of the arm 70, e.g., the halves can meet near where the extension 114 is coupled to the distal end 80 of the arm 70. The slots would allow the extensions 114 including the plates 120 to avoid the ridges of the shaft 50 during the retraction. In this manner, the ridges of the shaft 50 can be held against the sides of the vertebral bodies 210 during the retraction, to serve as guides to help the surgeon maintain the shaft 50 in place so that the implant 214 remains in place during the retraction.

It should also be noted that a benefit of not needing to prepare the vertebral bodies 210 or the space so that the implant 214 jams into the space so that the plates 120 can be removed is that the instrument of the invention in this embodiment and other embodiments does not rely on the structural integrity of the implant 214 for effective functioning of the instrument. Therefore, implants that are designed to have structural stability when finally inserted in between vertebral bodies, but which do not have a structure capable of withstanding the insertion forces, can be inserted using this embodiment and other embodiments of the invention. In addition, the risk of structural collapse (and possibly dangerous fragmentation) of the implant 214 is minimized by this embodiment and other embodiments of the invention.

In some cases, in order to fully insert the plates 120 and the implant 214 between the vertebral bodies 210, it will be necessary for the surgeon to apply greater and/or sharper force than can be provided manually. For example, the surgeon may need to use a hammer to tap the plates 120 and implant 214 in between the vertebral bodies 210. In such a case, because of the coupling between the body 180 and the proximal ends 74 of the arms 70, the surgeon can hinge the body 180 relative to the arms 70 to position the trunk 190 to allow access to the proximal ends 74 of the arms 70. Then, the surgeon can tap the proximal ends 74 of the arms 70 with the hammer to move the plates 120 and the implant 214 further in between the vertebral bodies 210.

Figure 18:
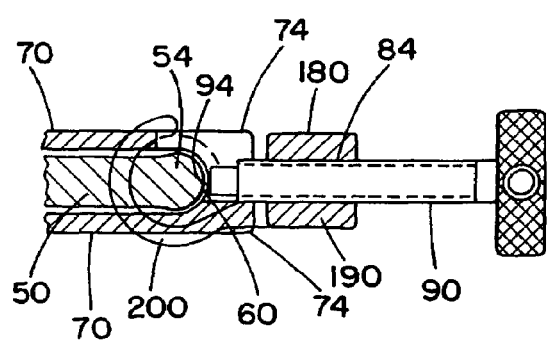
FIG. 18 shows an exemplary engagement of the distal end of the screw with the engagement surface of the shaft.

Once the plates 120 and the implant 214 are inserted between the vertebral bodies 210, the surgeon operates the instrument to pull the plates 120 out from between the vertebral bodies 210 while preventing the implant 214 from exiting from between the vertebral bodies 210. The bore 84 should be in longitudinally fixed relation to the arms 70 during the retraction. Also, the longitudinal axis of the bore 84 should be coaxial with the longitudinal axis of the shaft 50 during the retraction. Therefore, if the trunk 190 has been positioned to allow access to the proximal ends 74 of the arms 70, the surgeon can hinge the body 180 to align the longitudinal axis of the bore 84 coaxial with the longitudinal axis of the shaft 50. Because of the engagement of the hooks 200 with the passageways 194, this also places the bore 84 in longitudinally fixed relation to the arms 70, as best shown in FIG. 18.

The distal end 94 of the screw 90 should engage the engagement surface 60 of the proximal end 54 of the shaft 50 during the retraction. Therefore, if the screw 90 is not already in the bore 84, the surgeon inserts the screw 90 into the bore 84 and rotates the screw 90 within the bore 84 until the distal end 94 of the screw 90 engages the engagement surface 60, as best shown in FIG. 18.

As illustrated in FIGS. 19-20, rotation of the screw 90 within the bore 84, after the insertion of the implant 214 between the vertebral bodies 210 and once the distal end 94 of the screw 90 has engaged the engagement surface 60, effects the retraction by pulling the arms 70 alongside the shaft 50 until the distal ends 80 of the arms 70 no longer hold the implant 214. During the retraction, the distal end 64 of the shaft 50 can engage the implant 214 to prevent the implant 214 from being removed from between the vertebral bodies 210. The curvature of the distal end 64 of the shaft 50 helps to stabilize the implant 214 so that the implant 214 does not move laterally during the retraction. Accordingly, as the surgeon continues rotating the screw 90 while the distal end 94 of the screw 90 engages the engagement surface 60, the trunk 190 begins to move longitudinally with respect to the shaft 50, toward the head 92 of the screw 90, pulling the arms 70 with it using the hooks 200. As the arms 70 are pulled, the plates 120 are pulled and the implant 214 may be urged in the pulling direction due, e.g., to friction between the plates 120 and the implant 214. Because the distal end 64 of the shaft 50 can engage the implant 214 to remain fixed relative to the implant 214 while the plates 120 are pulled from between the vertebral bodies 210, it can prevent the implant 214 from being removed from between the vertebral bodies 210 with the plates 120.

Once the plates 120 are dear of the vertebral bodies 210, the surgeon removes the instrument from the treatment site and the patient's body and closes the wound.

While there has been described and illustrated particular embodiments of instruments for inserting implants between vertebral bodies, it should be understood that numerous variations and modifications are possible without deviating from the broad spirit and scope of the invention.

What is claimed is:

1. An instrument for inserting an implant between vertebral bodies, comprising:
    a holder adapted to hold the implant during insertion of the implant between the vertebral bodies, the holder including a plurality of arms having distal ends and extensions hingedly connected to the distal ends of the plurality of arms;
    a retractor adapted to retract the holder away from the implant after the insertion; and
    a guard adapted to prevent the implant from being removed from between the vertebral bodies during the retraction, wherein the retractor comprises a coupling adapted to couple the holder to the guard and by which relative movement between the holder and the guard is effectable during the retraction, and wherein the guard comprises a shaft adjacent the arms, the shaft having an engagement surface; and
the retractor comprises a threaded bore and a screw that is threadable within the bore, the screw having an end that engages the engagement surface of the shaft.

2. An instrument for inserting an implant between vertebral bodies, comprising:
    a holder adapted to hold the implant during insertion of the implant between the vertebral bodies, the holder including a plurality of arms having distal ends and extensions hingedly connected to the distal ends of the plurality of arms;
    a retractor adapted to retract the holder away from the implant after the insertion; and a guard adapted to prevent the implant from being removed from between the vertebral bodies during the retraction, wherein the retractor comprises a coupling adapted to couple the holder to the guard and by which relative movement between the holder and the guard is effectable during the retraction, and wherein the guard comprises a shaft having a proximal end and a distal end;

the plurality of arms being adapted to cooperate to hold the implant using the extensions hingedly connected to the distal ends of the arms such that the implant is adjacent the distal end of the shaft; and the retractor comprises a bore and a screw that can thread within the bore and engage the proximal end of the shaft.

3. The instrument of claim 2, wherein rotation of the screw within the bore effects the retraction by pulling the arms alongside the shaft.

4. The instrument of claim 3, wherein during the retraction, the distal end of the shaft is engageable with the implant to prevent the implant from being removed from between the vertebral bodies.

5. An instrument for inserting an implant between vertebral bodies, comprising:
   a holder adapted to hold the implant during insertion of the implant between the vertebral bodies, the holder including a plurality of arms having distal ends and extensions hingedly connected to the distal ends of the plurality of arms;
   a retractor adapted to retract the holder away from the implant after the insertion; and
   a guard adapted to prevent the implant from being removed from between the vertebral bodies during the retraction, wherein the retractor comprises a coupling adapted to couple the holder to the guard and by which relative movement between the holder and the guard is effectable during the retraction, wherein the guard comprises a shaft having a longitudinal axis, a proximal end having an engagement surface, and a distal end; and
   the plurality of arms each having a proximal end and the distal end and each longitudinally extending alongside the shaft, the arms being adapted to cooperate to hold the implant using the distal ends of the arms such that the implant is longitudinally adjacent the distal end of the shaft during insertion of the implant between the vertebral bodies, and wherein the retractor comprises a bore in longitudinally fixed relation to the arms during the retraction and having a longitudinal axis coaxial with the longitudinal axis of the shaft during the retraction, and a screw that can thread within the bore and having a distal end that can engage the engagement surface of the proximal end of the shaft during the retraction.

6. An instrument for inserting an implant between vertebral bodies, comprising:
   a holder adapted to hold the implant during insertion of the implant between the vertebral bodies, the holder including a plurality of arms having distal ends and extensions hingedly connected to the distal ends of the plurality of arms;
   a retractor adapted to retract the holder away from the implant after the insertion; and
   a guard adapted to prevent the implant from being removed from between the vertebral bodies during the retraction, wherein the retractor comprises a coupling adapted to couple the holder to the guard and by which relative movement between the holder and the guard is effectable during the retraction, and wherein the holder comprises a set of tongs adapted to hold the implant;

the guard comprises a central rod about which the set of tongs open and close; and the retractor comprises a screw assembly for retracting the set of tongs away from the implant while maintaining the rod against the implant to prevent the implant from being removed from between the vertebral bodies.

7. The instrument of claim 6, wherein the screw assembly comprises a bore and a screw that is rotatable within the bore to engage the rod during the retraction and move the set of tongs relative to the shaft.

8. An instrument for inserting a implant between vertebral bodies, comprising:
   a set of tongs having a proximal end and distal ends adapted to hold the implant during the insertion of the implant between the vertebral bodies;
   a central rod about which the set of tongs can open and close, having a proximal end and a distal end in front of which the distal ends of the set of tongs can hold the implant during the insertion, the rod being coupled to the set of tongs to prevent lateral movement between the rod and the set and allow longitudinal movement between the rod and the set; and
   a screw assembly at the proximal end of the set of tongs adapted to retract the distal ends of the set of tongs away from the implant after the insertion while allowing the distal end of the rod to be maintained against the implant during the retraction to prevent the implant from being removed from between the vertebral bodies during the retraction, wherein the rod is coupled to the set of tongs by a coupling comprising a lateral through slot through the rod that extends longitudinally within the rod, and a pin on the set of tongs that passes laterally through the through slot and travels longitudinally within the through slot during the retraction.

* * * * *